United States Patent [19]

Goodwin et al.

[11] Patent Number: 4,763,521
[45] Date of Patent: Aug. 16, 1988

[54] METHOD AND APPARATUS FOR DETERMINING WELDABILITY OF THIN SHEET METAL

[75] Inventors: Gene M. Goodwin, Lenoir City; Joseph D. Hudson, Knoxville, both of Tenn.

[73] Assignee: The United States of America as represented by the United States Department of Energy, Washington, D.C.

[21] Appl. No.: 846,529

[22] Filed: Mar. 31, 1986

[51] Int. Cl.⁴ .......................... B21D 7/04; B23K 20/08
[52] U.S. Cl. ........................................ 73/159; 73/834; 228/103
[58] Field of Search ............... 228/103, 104, 56.5; 73/159, 760, 761, 768, 774, 781, 799, 834

[56] References Cited

U.S. PATENT DOCUMENTS

| 2,600,029 | 6/1952 | Stone | 73/761 |
| 3,201,977 | 8/1965 | Kutsay | 73/761 |
| 3,645,130 | 2/1972 | Million et al. | 73/834 |
| 4,569,126 | 2/1986 | Weber | 29/407 |

FOREIGN PATENT DOCUMENTS

| 2840630 | 3/1980 | Fed. Rep. of Germany | 73/834 |
| 633691 | 11/1978 | U.S.S.R. | 228/103 |
| 659323 | 6/1979 | U.S.S.R. | 228/103 |
| 703274 | 12/1979 | U.S.S.R. | 228/103 |
| 716744 | 2/1980 | U.S.S.R. | 228/103 |
| 761201 | 9/1980 | U.S.S.R. | 228/103 |
| 836552 | 6/1981 | U.S.S.R. | 73/834 |

OTHER PUBLICATIONS

"The Varistraint Test" by C. D. Lundin, et al., Bulletin 280, Aug. 1982, Welding Research Council, United Engineering Center.

Primary Examiner—William A. Cuchlinski, Jr.
Assistant Examiner—W. Morris Worth
Attorney, Agent, or Firm—Earl L. Larcher; Stephen D. Hamel; Judson R. Hightower

[57] ABSTRACT

A fixture is provided for testing thin sheet metal specimens to evaluate hot-cracking sensitivity for determining metal weldability on a heat-to-heat basis or through varying welding parameters. A test specimen is stressed in a first direction with a load selectively adjustable over a wide range and then a weldment is passed along over the specimen in a direction transverse to the direction of strain to evaluate the hot-cracking characteristics of the sheet metal which are indicative of the weldability of the metal. The fixture provides evaluations of hot-cracking sensitivity for determining metal weldability in a highly reproducible manner with minimum human error.

12 Claims, 4 Drawing Sheets

METHOD AND APPARATUS FOR DETERMINING WELDABILITY OF THIN SHEET METAL

This invention was made as a result of work under a contract DE-AC05-84OR21400 between Martin Marietta Energy Systems and the U.S. Department of Energy.

BACKGROUND OF THE INVENTION

The present invention relates generally to the hot-cracking sensitivity of thin sheet metal during welding to determine the weldability of the metal. More particularly the present invention is directed to the method and apparatus for applying preselected stress loadings to the sheet metal prior to and in the direction transverse to the direction of welding in order to determine the weldability of the sheet metal by evaluating the sensitivity of the metal to hot cracking at various stress loadings.

The weldability of sheet metal formed of essentially the same alloy composition has been found to differ from heat-to-heat and by using different welding process variables such as current, arc spacing and welding speed so as to produce various welding defects. These welding defects include hot cracking with the cracks ranging in size from microcracks in the welding area to separation of the sheet metal along the weldment. The tendency for hot cracking during welding is primarily influenced by the metallurgical characteristics of the alloy. The formation of a crack in a weldment requires that material comprising the weldment exhibit a phase or combination of phases and possess a limited capacity to tolerate strain within some critical range of temperatures and that the strain imposed upon the weldment by the combined action of thermal and restraint conditions within this critical range of temperatures exceeds the strain tolerance of the composite microstructural region. Other weldment defects such as cold cracking, slagging, poor fusion, porosity, and the like are primarily caused by welding process variables.

In determining the weldability of sheet metal, it has been found that the sensitivity of the sheet metal to hot cracking during welding to be a satisfactory technique for evaluating the weldability of sheet metal. Ideally a hot-cracking test for determining the weldability of sheet metal would have the capability to show a direct correlation with the actual fabrication and service behavior and the reproducibility of results with freedom from variations due to operator skills. The criteria for such a test should also include a high level of sensitivity to small changes in test variables and the ability to show the effects of several welding variables as well as applicability to all welding processes utilized for sheet metal.

Several techniques have been previously utilized for determining the weldability of sheet metal formed of various alloy compositions. Generally, the sensitivity of the sheet material to hot cracking during welding has been determined by employing a so-called "VARESTRAINT" test. This test is a variable restraining test developed by Rensselaer Polytechnic Institute, Troy, N.Y. and comprises mounting a rectangular specimen of sheet metal in a fixture in a cantilever manner. The specimen was then autogenously welded from the unsupported end and as the weld pool passed a certain longitudial point, a load was rapidly applied to the specimen to suddenly bend the specimen to conform to the curved surface of an underlying die block. This augmented strain applied during the welding is used to stress the specimen since the inherent restraint in the specimen is relatively small and too low to induce hot cracking. This level of augmented strain required to cause hot cracking in the specimen with a particular set of welding parameters provided an accurate measurement of the hot-cracking sensitivity. The variation in specimen heats as well as welding parameters cause cracking at different levels of augmented strains so as to provide reproducibility and quantitative methods for determining the weldability of various alloy compositions. Further details of this previous technique and variations thereof as well as details relating to hot-cracking characteristics of metals are set forth in the Welding Research Council Bulletin entitled "The Varestraint Test" by C. D. Lundin et al, Bulletin 280, Aug. 1982, available from the Welding Research Council, United Engineering Center, 345 East 47th St., New York, N.Y., 10017. This publication is incorporated hearin by reference.

Other techniques used for evaluating the hot-cracking sensitivity of sheet metal for determining the weldability of the metal include the so-called Lambert test and the ORNL test. Generally, in the Lambert test, a coupon composed of a prestressed sheet (100 mm wide×200 mm long) of say, type 304L stainless steel is butt welded to a sample of the same dimensions of the material to be evaluated. The overall length of the fabricated coupon is 400 mm long. The type 304L sheet is used as a standard and the test procedure consists of side-by-side autogenous welds provided by a gas-tungsten-arc (GTA) welding process which provides a moving pool of weld metal along the length of the test coupon. About 12 to 16 weld passes are used on each weld pad with two weld pads being provided per coupon. A dye penetrant is then used to indicate the presence of cracks in the sample. Details of the Lambert test are discussed in the publication "The Effect of Phosphorus, Sulfur, and Ferrite Content on Weld Cracking of Type 309 Stainless Steel," by J. A. Brooks and F. J. Lambert, Jr., Welding Journal, Volume 57(5), pages 139 to 143 (May 1978).

The ORNL test is described in assignee's U.S. Pat. No. 4,499,758 and generally comprises the mounting of a disc-shaped specimen in a test fixture. Two circular autogenous welds are made using the gas-tungsten-arc welding process. The welds are of different diameters and establish increasing restraint levels in the specimen. The specimen is then removed and turned 180° and a weld procedure for providing welds of the same diameter is repeated. The earlier weld procedure renders the microstructure of the material susceptable to cracking and also increases the residual stress within the material that could enhance the material suscepibility for cracking. This restraint may be varied to the extent that the top plate is clamped down.

While prior art techniques such as described above provide satisfactory evaluation of hot-cracking sensitivity for determining the weldability of various alloy compositions there are some shortcomings or drawbacks which detract from their usefulness. For example, with previous techniques, such as the Varestraint test, as described above, thin sheet material less than about 0.125-inch thickness could not be ranked while the Lambert weldability test, which was capable of ranking thin sheet material, was highly operator sensitive as to introduce an undesirable level of errors from test-to-test and operator-to-operator. In the ORNL test, as described above in the aforementioned patent, the problems include limits on the restraint which can be applied (limited to self-restraint of the specimen) and the nonquantitative measure of cracking sensitivity which results.

SUMMARY OF THE INVENTION

It is an aim or objective of the present invention to provide for a highly reproducible and accurate evaluation of hot-cracking sensitivity of thin sheet metal during welding for determining the weldability thereof with minimal operator error.

Another object of the present invention is to provide an apparatus for the evaluation of hot-cracking sensitivity of thin sheet material with the apparatus having the capability of applying a preselected stress loading to the sheet material prior to welding thereof.

A further object of the present invention is to provide an apparatus and method for evaluating the hot-cracking sensitivity of thin sheet material with sufficient sensitivity to detect minor differences in heat-to-heat compositions of the same alloy.

Generally, the present invention determines the weldability of sheet metal by evaluating the hot-cracking sensitivity of the metal by the steps comprising applying a preselected stress to the sheet of the metal in a first direction and thereafter directing a pool of weld metal across the sheet in a second direction transverse to the direction of applied stress. The minimum level of stress required to induce hot-cracking with a given set of welding parameters provides a quantitative index of hot-cracking sensitivity referred to as the cracking threshold. This cracking threshold can be changed by variations in the welding process and welding parameters and thus also provides a quantitative index for comparing different welding procedures. Cracking threshold is the minimum stress required to effect hot cracking. Since in the practice of the present invention the stress load ($\sigma$) is applied in a direction transversly to the direction of the welding the minimum stress required for the initiation of hot-cracking is referred to herein as the $\sigma_{min}$ stress.

The apparatus for evaluating the hot-cracking sensitivity of thin sheet metal of a thickness in the range of about 0.005 to 0.125 inch to determine the weldability of the metal comprises a base with first and second coextensive jaw support means secured to a planar surface on the base with the second jaw support means being moveable thereon with respect to the first jaw support means. Jaw or grip means are carried by the first and second jaw support means for securing a sheet of metal to be welded for evaluating the hot-cracking sensitivity thereof. The sheet of metal extends over a space between the jaw support means along a plane coplanar with the planar surface on the base. Load inducing means are coupled to the second jaw support means for urging or moving the second jaw support means away from the first jaw support means to stress the sheet of metal in a direction transverse to the direction of welding. Adjusting means are associated with the load inducing means for selectively varying the applied stress on the sheet of metal prior to welding.

The weldability test is sufficiently sensitive to detect heat-to-heat differences and permits the application of preselected stresses to the specimens prior to welding so as to provide a highly reproducible and accurate evaluation of hot-cracking sensitivity of various alloy compositions. The present apparatus is operable in such a manner as to introduce minimal operator error and is readily applicable for field use to determine the weldability of metals in the highly reproducible manner prior to any particular welding operation.

Other and further objects of the invention will be obvious upon an understanding of the illustrative emodiments and method about to be described or will be indicated in the appended claims and various advantages not referred to herein will occur to one skilled in the art upon the employment of the invention in practice.

A prefered embodiment of a present invention has been chosen for the purpose of illustration and description. The prefered embodiment illustrated is not intended to be exhaustive or to limit the invention to precise form disclosed. It is chosen and described to best explain the principles of invention and their application in practical use to thereby enable others skilled in the art to best utilize the invention in various embodiments and modifications as are best adapted to the particular use contemplated.

DETAILED DESCRIPTION OF THE INVENTION

As generally described above, the invention is directed to the method and apparatus for determining the weldability of sheet metal by evaluating the hot-cracking sensitivity of the sheet metal. The method is practiced by the steps of securing a sheet of metal between relatively moveable grips. A directional load of a preselected value is applied to one of the grips to stress or strain the sheet of metal in one direction. A weld pool is established at one edge of the sheet of metal and moved across the sheet of metal in a direction transverse to the direction of the applied strain. The sensitivity of the metal to hot-cracking at a selected strain is a reproducible index indicative of the weldability of the sheet metal.

Figure 1:
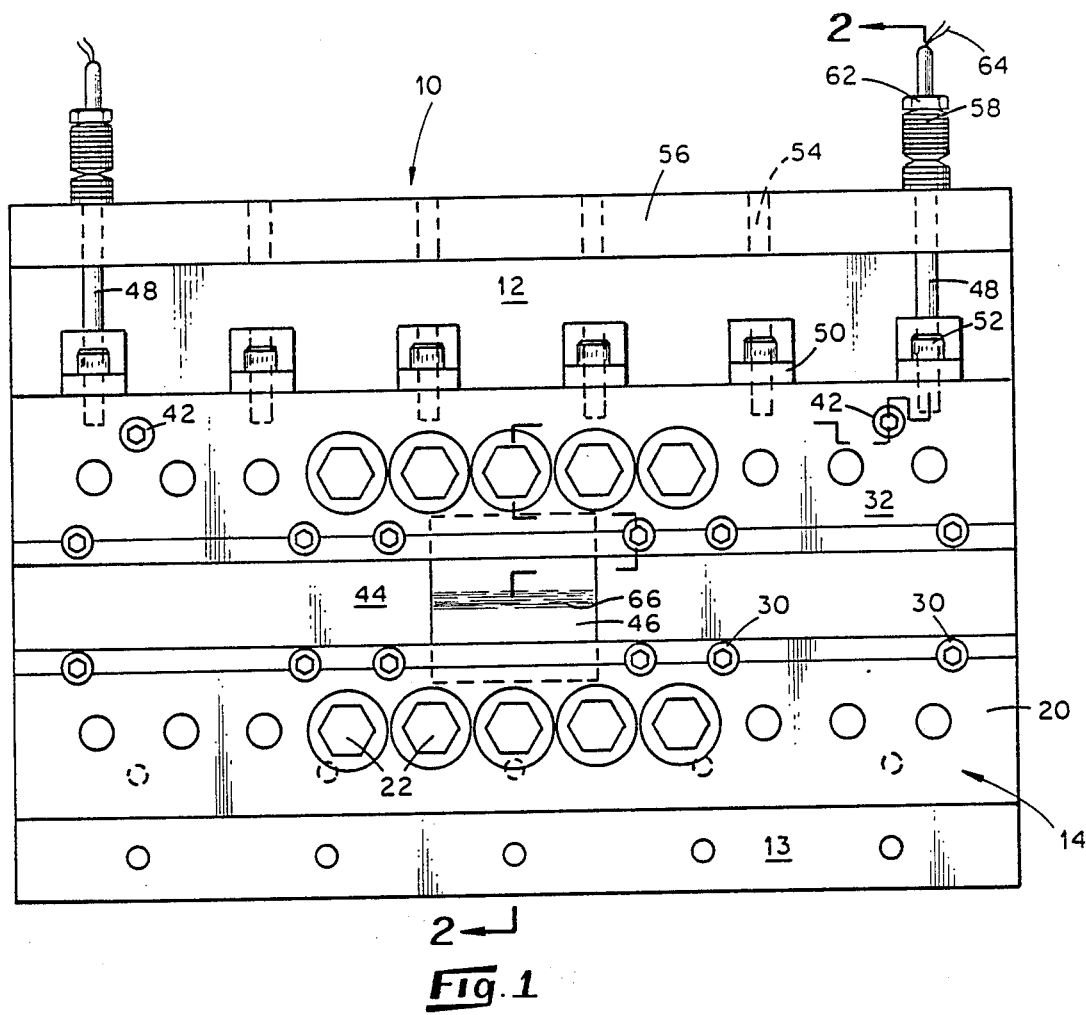
FIG. 1 is a plan view of the apparatus of the present invention utilized for evaluating hot-cracking sensitivity of thin sheet material for determining the weldability thereof.
Figure 2:
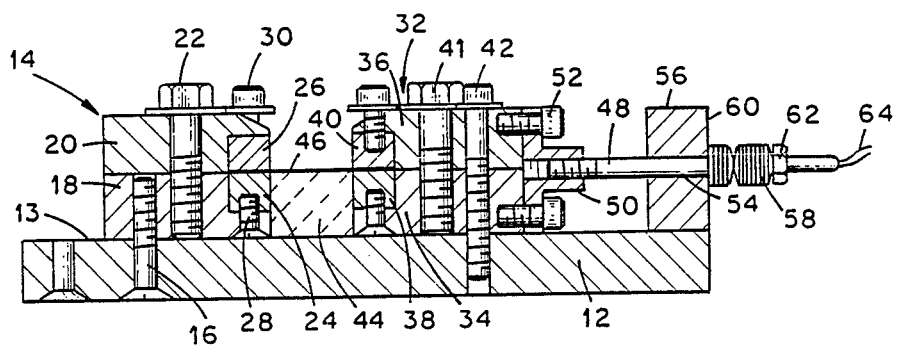
FIG. 2 is a sectional view taken along the lines 2—2 of FIG. 1 showing details of the apparatus of FIG. 1.

The apparatus for providing this evaluation of hot-cracking sensitivity is shown in FIGS. 1 and 2 as a fixture 10 which comprises a base 12 of a rectangular configuration with a planar upper surface 13. A two-piece jaw support 14 of an elongated rectangular configuration is disposed on the planar surface 13 of the base and is secured thereto by bolts 16. The jaw support is formed of upper and lower plates or segments 18 and 20 coupled together by bolts 22. Five of these bolts 22 are shown for providing a secure clamping arrangement for the sheet-metal specimen to be stressed, as will be described below, but any suitable number of bolts 22 may be utilized. The jaw support 14 is used for supporting and operating replacable jaws or grips 24 and 26 carried by and affixed to the segments 18 and 20 respectively by bolts 28 and 30. The grips 24 and 26 are provided with knurled opposing surfaces for securely gripping a sheet-metal weld test specimen positioned therebetween upon the tightening of the bolts 22.

A second two-piece jaw support 32 of a rectangular configuration is positioned on the planar surface 13 of the base 12 in an orientation parallel with but transversely spaced from the first jaw support 14. As with jaw support 14 the jaw support 32 is formed of lower and upper plates or segments 34 and 36 and jaws or grips 38 and 40 which are similar to the jaw segments and grips of jaw support 14. A plurality of bolts 41 are used for coupling the jaw support segments 34 and 36 together and for clamping the weld test specimen between grips 38 and 40. The grips 24 and 26 on jaw support 14 and the grips 38 and 40 on jaw support 32 are shown facing one another across the space therebetween so that the specimen may be positioned in and span the space between the jaw supports 14 and 32. While the jaw supports 14 and 32 are shown as being coextensive with the base 12, it will appear clear that the jaw supports may be of different lengths than the base 12 if desired.

The jaw support 32 is bolted to the base 12 by bolts 42 (two bolts 42 are shown) and are used for holding the jaw support in position during the mounting of the weld test specimen in the fixture 10. These bolts 42 are removed prior to the stressing of the specimen which is provided by the relative displacement of jaw support 32 with respect of the jaw support 14 in a direction coplanar with the planar surface 13 on the base 12.

A block 44 of highly conductive metal or heat resistant refractory metal or ceramic material is disposed in the space between the jaw supports 14 and 32, as shown, with this block of material being of a width corresponding to the desired spacing between the jaw supports 14 and 32. The block 44 is also of a thickness corresponding to the thickness of the segments 18 and 34 of the jaw supports 14 and 32 respectively so that the upper surface of the block 44 and the plane defined between the upper and lower segments of each jaw support are coplanar with the plane 13 of the base 10 so as to assure that the specimen 46 will be disposed in and stressed along a plane parallel with the base surface 13. The sheet metal weld test specimen 46 is shown of a generally square configuration and is mounted in the fixture 10 in the plane coplanar with the base surface 13 by removing or suitably loosening bolts 22, 41 and 42. With the specimen 46 properly positioned between the grips of the jaw supports 14 and 32 the bolts 22 and 41 are securely tightened to rigidly clamp the specimen 46 in place. With the specimen so clamped, bolts 42 may be removed so that the jaw support 32 may be moved relative to jaw support 14 for stressing the test specimen 46. As shown, the fixture 10 is provided with additional bolt-receiving bores so that specimens of different sizes may be mounted in the fixture and evaluated for hot-cracking sensitivity.

In order to apply the desired stress loading on the weld test specimen 46, for obtaining the hot-cracking sensitivity measurements, at least two load cells provided by strain-gaged bolts 48 are attached to a bracket 50 affixed to the jaw support 32 in any suitable manner such as by bolts 52. The strain-gaged bolts 48 also pass through bores 54 in an elongated flange 56 fixedly attached to a longitudinal edge of the base 12. As shown, the flange 56 is coextensive with the base 12 and jaw supports 14 and 32 and is provided with a plurality of longitudinally spaced apart bores 54 for receiving additional strain-gaged bolts 48 or for positioning the strain-gaged bolts 48 in different preselected locations. The stress load on the weld test specimen 46 is provided prior to welding by the use of stacked sets of Belleville washers 58 which are positioned between a face 60 on flange 56 and bolt head 62 on the strain-gaged bolts 48. The Belleville washers 58 are arranged in stacked sets defined by a plurality of washers oriented in one direction with a plurality of washers disposed in the opposite direction bearing thereagainst. The use of these stacked sets of Belleville washers for the stress applying load train provides an adjustable spring constant and thereby avoids the inherent limitations of applying dead weight loads as in the afore described prior art techniques. The spring constant permits a relaxation of reapplied load during motion of the weld pool across the sheet specimen due to yielding and thermal expansion of the specimen.

The stress load on the sample or specimen 46 is provided by rotating the strain-gaged bolts 48 to screw the strain-gaged bolts 48 into or out of the the threaded bracket 50 so that the load provided by the washers 58 on the support 32 increases or decreases the strain on the specimen 46. Also by varying the size of the sets or the number of sets of Belleville washers in each stack the stress loading on the specimen 46 can be accurately adjusted over a wide range. This stress loading system was calibrated with strain-gage specimens and was found to have a repetitive accuracy of ±0.1 percent and a resolution of 1 pound of load.

A signal generated by the strain placed upon the specimen 46 is transmitted by leads 64 on the strain-gaged bolts 48 to a strip recorder or the like (not shown) so that the strain loadings on the specimen 46 prior to the welding can be applied in an accurate and repetitive manner, and monitored as the test is performed.

After the weld test specimen 46 is clamped in the fixture 10 and a selected stress load applied to the weld test specimen 46, a weld such as generally shown at 66 is provided along the centerline of the specimen 46 in the direction parallel to the longtitudinal length of the jaw supports 14 and 32 and perpendicular or transverse $\sigma$ to the direction of the applied stress. The welding is normally an autogenous weld as provided by any of various weld processes such as gas-tungsten-arc, laser, plasma, or electron beam processes. However, the present invention can also be utilized for testing the weldability of alloys by using filler metal weldments. In such instances a specimen without the induced stress loading is provided with a bead of filler metal over the length thereof. The filler metal is ground to a level near the surface of the specimen 46. The specimen 46 is then mounted and stressed in the fixture 10 in a manner similar to that used for the autogenous welding procedure and a weld pool is provided by a suitable autogenous welding technique along the length of the specimen over the filler metal weldment to provide for the evaluation of the hot-cracking sensitivity of the alloy with the filler metal weld.

In using the fixture of the present invention, specimens of the same heat are subjected to increased stress loadings a specimen at a time until a minimum level of stress ($\sigma_{min}$) is attained where center line cracking is initiated. The testing of each specimen of a given heat is provided by employing the same welding process and utilizing the same welding parameters such as current, arc length, and travel speed so that the results can be uniform for each specimen at each of the successive stress loadings. Of course, as will be described below the welding parameters can be varied on similarly stressed specimens to determine the weldability of the specimen material when subjected to different welding parameters suitable for welding a particular alloy.

testing of these specimens was performed by a two step procedure. In the first step, six specimens of each heat were tested in random order in a range of about 25 to 50 ksi loads applied at 5 ksi intervals. In the second step, the stress intervals were further subdivided.

TABLE

Composition of 0.25-mm-thick stainless steels

| Heat | Type | Composition (wt. %) | | | | | | | | | | Cracking Response $\sigma$ min. ksi |
|------|------|-----|------|------|------|-----|-------|-------|------|-----|------|-----|
|      |      | C   | Mn   | P    | S    | Si  | Ni    | Cr    | Mo   | Cu  | N    |     |
| 9937 | 304 | .015 | 1.38 | .030 | .008 | .52 | 8.33 | 18.15 | .17 | .22 | .085 | 45 |
| 9938 | 304 | .013 | 1.34 | .025 | .008 | .52 | 8.37 | 18.25 | .17 | .22 | .082 | 45 |
| 11124 | 304 | .012 | 1.35 | .034 | .004 | .49 | 9.15 | 18.12 | .18 | .32 | .094 | 37 |
| 10749 | 304 | .022 | 1.38 | .035 | .004 | .63 | 9.11 | 18.17 | .32 | .44 | .104 | 49 |
| 11352 | 304 | .015 | 1.36 | .032 | .002 | .69 | 9.19 | 18.25 | .23 | .32 | .074 | 53 |
| 9643 | 304 | .014 | 1.37 | .030 | .010 | .48 | 8.29 | 18.48 | .16 | .22 | .082 | 35 |
| 59449 | 316 | .018 | 1.70 | .033 | .010 | .34 | 12.32 | 17.25 | 2.00 | .06 | .041 | 20 |
| 828013 | 316 | .018 | 1.70 | .032 | .010 | .34 | 12.16 | 17.04 | 1.98 | .05 | .047 | 18 |
| 12 | 316 | .020 | 1.76 | .042 | .009 | .61 | 11.35 | 16.87 | 2.12 | .46 | .048 | 15 |
| 730693 | 316 | .022 | 1.78 | .034 | .002 | .60 | 11.07 | 17.38 | 2.15 | .35 | .041 | 42 |
| 13301 | 316 | .050 | .01 | .003 | .003 | .03 | 13.56 | 17.53 | 2.51 | .01 | .052 | 36 |
| 191513 | 316 | 0.049 | 1.63 | .020 | .003 | .77 | 10.50 | 16.89 | 1.99 | .05 | .040 | 50 |

Figure 3:
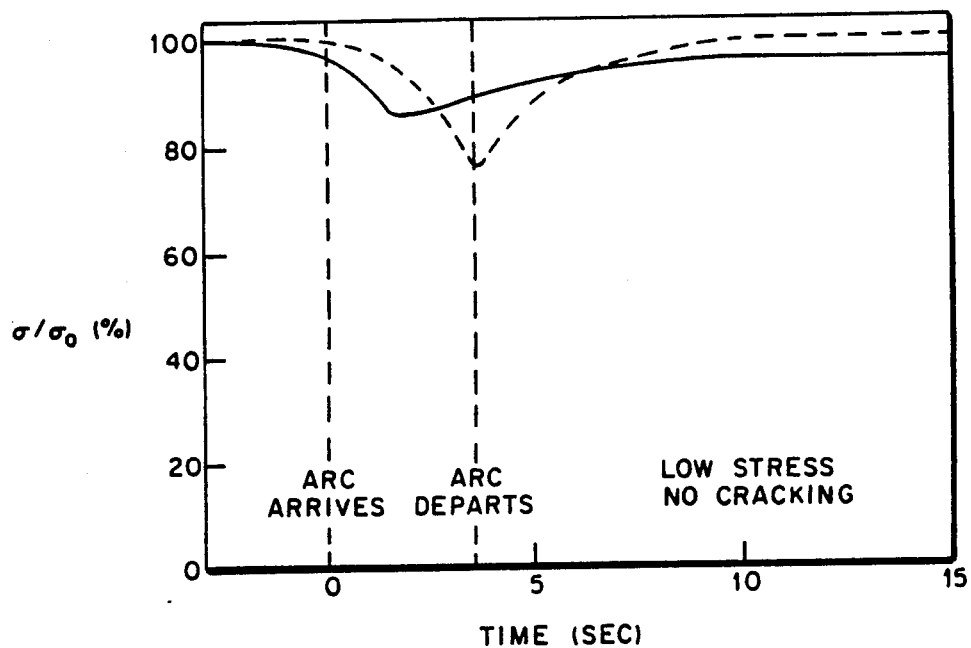
FIGS. 3-6 are graphs or plots illustrating various behaviors of specimens during welding in the fixture of the present invention.
Figure 4:
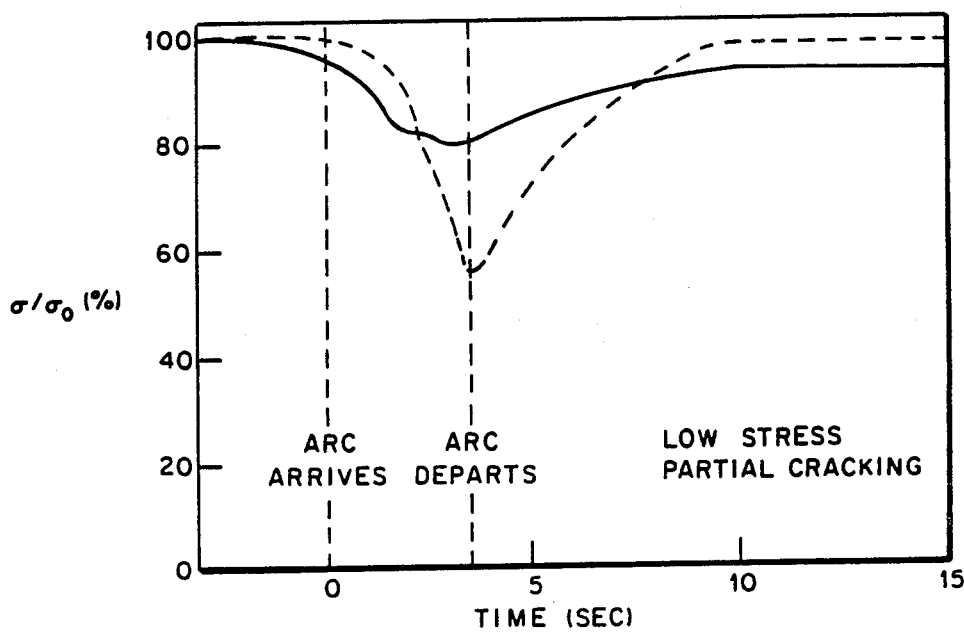
Figure 5:
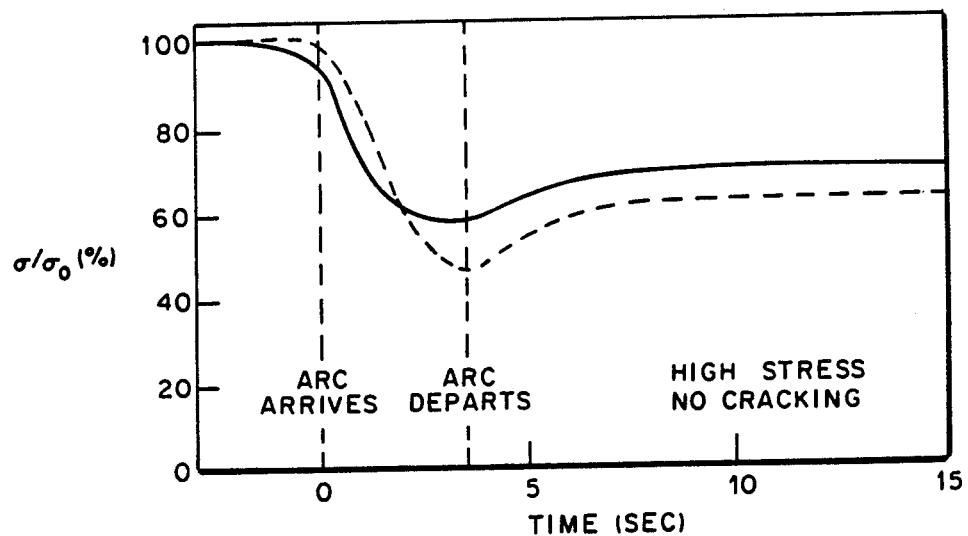
Figure 6:
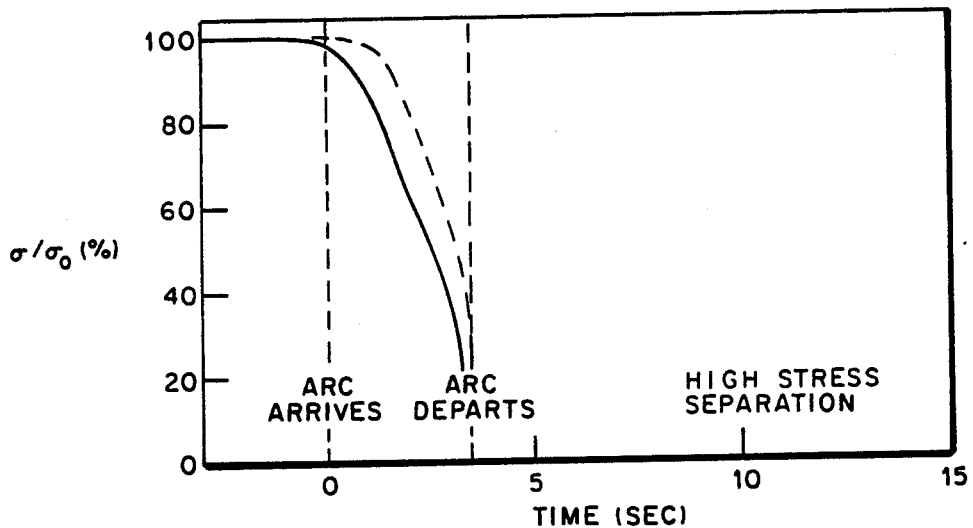

In a typical operation with the fixture 10 of the present invention as illustration in FIGS. 3–6 where plots are provided which graphically illustrate signals derived from two load cells positioned on the fixture as in FIG. 1. These plots from each of the two load cells are time related as a weld progresses across a specimen stressed at different levels as indicated in FIGS. 3–6. Also, in FIGS. 3–6, the load on the load cell on the starting side of the specimen is shown as a solid curve while the load on the load cell on the finishing side of the specimen is shown as a dashed curve. In FIG. 3, with the specimen at low stress and no cracking, the first load cell responds as the arc approaches the specimen shown between the vertically dotted lines. The stress provided by the first load cell drops to a minimum value when the arc is approximately half way across the specimen and then recovers to essentially the starting load when the specimen cools. As shown the second load cell responds to stress later than the first load cell and reaches a lower minimum value but recovers similarly as the specimen cools. In FIG. 4, a different stress level is used with partial hot-cracking present. With the first load cell the onset of cracking is shown as a secondary dip after the initial minimum stress has been reached. In FIG. 5, a high stress load is applied with no cracking but considerably more yielding occurs in the specimen and stress loads recover only a fraction of their initial value. In instances where a separation of the specimen occurs as in FIG. 6, both load cells monotonically decrease to zero as the specimen separation occurs. As suggested by these plots the amount of yielding that a specimen undergoes is a function of the pre-applied stress. The thermal expansion and contraction of the samples are essential free from heat-to-heat variations within a given class of materials. If the stress applied to the specimen is sufficiently high, cracking will be initiated at the start of the weld (100 percent cracking), or cracking will not be initiated until the loading has shifted substantially from the second load cell back to the first load cell as the weld progresses.

Figure 7:
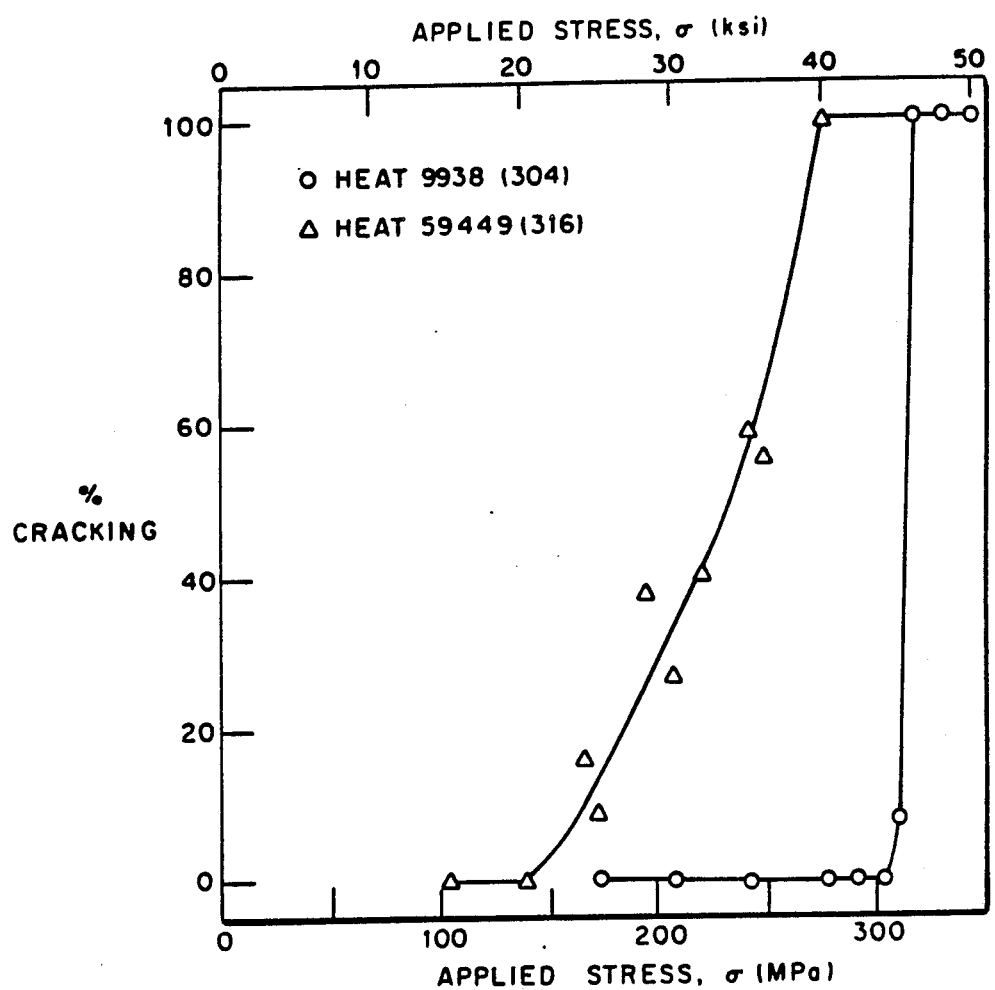
FIG. 7 is a graph illustrating the percent of hot cracking defined as a function of specimen length cracked versus applied stress for two different alloy compositions.

In a demonstration of the present invention twelve heats of 0.25 mm thick austenitic stainless steel types 304 and 316 (six of each type) were evaluated. With the exception of heat 13301, which is a high purity laboratory heat, all were commercial heats and the compositions of these heats are listed in the Table below. The The cracking data provided two generally different catagories of cracking as typified by the type 304 stainless steels as compared to the type 316 stainless steels as shown in FIG. 7 which illustrates the percent cracking defined as a fraction of the specimen length cracked versus applied stress. The crack length can be measured on a specimen by using a ruler or an overhead projector. Some heats, such as heat 9938 (type 304) show no cracking until very high stress levels of greater than 40 ksi are reached and then show a sharp transition within 0–2 ksi to 100 percent cracking or specimen separation. As shown in FIG. 7 another heat, 59449 (type 316) shows the onset of cracking ($\sigma_{min}$) at substantially lower stress levels than for heat 9938 followed by a relatively gradual transition to 100 percent cracking. The reproducability of this hot cracking demonstration was verified by repeated testing of heat 828013 (type 316) over a six month period. With a total of 36 runs at a strain loading of 30 ksi, the average cracking was 40.3 percent with the standard deviation of 9.7 percent. The range was from 23 to 59 percent cracked.

The Table also lists the cracking response of the specimens by determining the minimum stress ($\sigma_{min}$) at the level at which the center line cracks are initiated at the trailing edge of the weld pool. In some highly crack resistant materials such as type 304 stainless steels, the crack initiation coincides with the stress at which complete specimen separation occurs. For the type 304 stainless steels as typified in FIG. 7, there is no apparent coorelation between the minimum stress and any of the usual chemical and microstructural variables. The phosphorous and sulfur contents of these heats are within a narrow range (0.033–0.040 weight percent) for all heats. The Cr/Ni ratios are all in an excess of 1.5 and all heats have a predicted ferrite number of at least 3 and solidify as primary ferrite. The belief that these heats should not crack is confirmed by observation of the cross section of the tested specimen in that each of the six type 304 stainless steel specimens was found to fail in tension with the reduction of area greater than 90 percent at an initial stress level greater than its annealed room-temperature yield strength. The room-temperature tensile yield strength values for all 12 heats listed in the Table range from 40.9–57.5 ksi as cold-worked and from 27.9-34.0 ksi annealed. The high temperature strength of these heats is commonly presumed to be proportional to the room temperature values. The resistance of type 304 stainless steels to hot-cracking until very high stress levels are reached results in a sharp transition from 0 to 100 percent cracking as shown in FIG. 7. In rare instances, where only partial cracking occurs such cracking invariably occurs at the start of the weld.

As also typified in FIG. 7, the type 316 stainless steel heats exhibit classical hot cracking. The reduction-of-area values are typically less than 30 percent and the transition from 0 to 100 percent cracking is gradual, especially for the lower values of the minimum stress. Partial cracking invariably occurs at the end of the weld. The type 316 stainless steels found to have the best hot-cracking sensitivity, as typified by heat 730693, possesed low phosphorous and sulfur levels, high Cr/Ni ratios, high predicted ferrite numbers, and solidification as primary ferrite. Alternatively, heat 13301 has a low phosphurus and sulfur level but possesses a very low Cr/Ni ratio and solidifies as primary austenite. This heat has a cracking sensitivity in the middle of the range of the six heats.

The above demonstration of the present apparatus and method shows that the present invention can be successfully utilized to rank various alloys in thin sheet configurations so as to provide a desirable index which will greatly facilitate the welding of alloys of different compositions and alloys having slight variations in heat-to-heat compositions. The fixture can be used to evaluate the hot-cracking sensitivity of alloy sheets in a thickness range of about 0.005 to 0.125 inch.

We claim:

1. A method for determining the weldability of sheet metal by evaluating hot-cracking sensitivity, comprising the steps of (1) applying a preselected stress to a sheet of metal of a selected heat in a first direction, (2) thereafter providing a pool of a weld metal and movement of said pool of weld across said sheet of metal in a second direction transverse to the direction of the applied stress, (3) monitoring for the presence of hot-cracking at said preselected stress as indicated by changes in the preselected stress in said sheet of metal during the movement of the pool of weld metal, and repeating steps 1 thru 3 on a plurality of sheets of metal of the same heat with each repetition of steps 1 thru 3 being at greater preselected stress until hot-cracking is initiated.

2. The method of claim 1, including the step of repeating steps 1 thru 3 on a plurality of sheets of metal of the same heat, and varying at least one of a plurality of the process parameters utilized for providing the pool of weld metal and the movement thereof across each of said plurality of sheets of metal.

3. The method claimed in claim 2, wherein said pool of weld metal is provided autogenously, and wherein said plurality of process parameters include arc current, arc spacing, and rate of movement of the pool of weld metal across said sheet of metal.

4. A method for determining the weldability of sheet metal by evaluating hot-cracking sensitivity, comprising the steps of (1) securing a sheet of metal of a selected thickness from a selected heat between two grips, (2) applying a directional load of a preselected value on one of the grips to effect movement thereof relative to the other of said grips to stress the sheet of metal at a predetermined level of stress, (3) establishing a pool of weld metal at one edge of said sheet of metal and moving the pool of weld metal across said sheet of metal in a direction transverse to the direction of the applied load (4) monitoring for the presence of cracking in said sheet of metal at said predetermined level of stress on said sheet of metal during the movement of said pool of weld metal to determine the hot-cracking sensitivity of said sheet of metal at said predetermined level of stress, and repeating steps 1 thru 4 on a plurality of sheets of metal of the same heat and thickness wherein with each repetition of steps 1 thru 4 each successive one of said plurality of sheets being provided with a greater predetermined level of stress until hot-cracking of the sheet metal is initiated.

5. Apparatus for evaluating the hot-cracking sensitivity of a sheet of metal during welding thereof by changes in a preselected stress applied on the sheet of metal prior to said welding to determine weldability of the metal, comprising a base, a first jaw support means secured to a planar surface on said base, second jaw support means supported on said planar surface of said base and movable thereon with respect to said first jaw support means, grip means carried by said first and second jaw support means for securing a sheet of metal to be autogenously welded thereacross between the first and second jaw means along a plane coplanar with said planar surface, load inducing means coupled to said second jaw support means for urging said second jaw support means away from said first jaw support means to stress said sheet of metal in a direction transverse to the direction of welding of said sheet of metal, adjusting means associated with said load inducing means for applying a preselected stress on said sheet of metal prior to welding, and load cell means coupled to said load inducing means for providing a signal indicative of changes in said preselected stress during welding of said sheet of metal.

6. The apparatus claimed in claim 5 wherein said load inducing means comprises a bias means for applying an adjustable spring constant loading on said sheet of metal.

7. The apparatus claimed in claim 6, wherein said bias means comprises stacked sets of Belleville washers.

8. The apparatus claimed in claim 7, wherein at least two of said load cell means are coupled to said second jaw support means at longitudinally spaced apart locations, wherein each of said load cell means comprises a strain-gaged bolt attached at one end thereof to said second jaw support means, wherein stacked sets of Belleville washers are disposed about each strain-gaged bolt at a location thereon adjacent an opposite end thereof and bear against said base during the stressing of said sheet of metal, wherein said adjusting means comprises moveable means carried by each of said strain-gaged bolts for coupling each strain-gaged bolt to said Bellville washers disposed thereabout, and wherein movement of said moveable means adjusts the load provided by said Belleville washers to vary the preselected stress on said sheet of metal.

9. The apparatus claimed in claim 6, wherein the first and second jaw means are of a rectangular configuration and are disposed on said base in a spaced apart and parallel orientation, each of said first and second jaw support means comprises upper and lower segments each supporting a portion of said grip means, wherein bolt means extend through said upper and lower segments for drawing together the portions of the grip means carried thereby for securing said sheet of metal in said grip means.

10. The apparatus claimed in claim 9, wherein a block is disposed between the first and second jaw support means for supporting the specimen.

11. The apparatus as claimed in claim 10, wherein elongated flange means are secured to said base and are provided with a plurality of longitudinally spaced apart passageways extending therethrough along a plane parallel with the planar surface on said base, wherein said load cell means comprises elongated strain-gaged bolts each extending through one of said passageways and secured at one end thereof to said second jaw support means, wherein at least two strain-gaged bolts are secured at one end thereof to said second jaw support means at longitudinally spaced apart locations, wherein said bias means is disposed between said flange means and an end of said strain-gaged bolts opposite said one end thereof secured to said second jaw support means for applying a load thereon for urging said second jaw support means away from said first jaw support means, and wherein said adjusting means varies the load on said second jaw support means.

12. The apparatus claimed in claim 11, wherein said bias means comprises a plurality of Belleville washers disposed about each of said strain-gaged bolts.

* * * * *